US00PP28176P2

(12) United States Plant Patent
Hansen

(10) Patent No.: US PP28,176 P2
(45) Date of Patent: Jul. 11, 2017

(54) ***BUDDLEIA* PLANT NAMED 'ORCHID ANNIE'**

(50) Latin Name: *Buddleia davidii*
Varietal Denomination: Orchid Annie

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 14/999,593

(22) Filed: May 31, 2016

(51) Int. Cl.
*A01H 5/00* (2006.01)

(52) U.S. Cl.
USPC ..... Plt./242

(58) Field of Classification Search
USPC ..... Plt./242
See application file for complete search history.

*Primary Examiner* — Annette Para

(57) ABSTRACT

*Buddleia* 'Orchid Annie' is a very short, compact, round-mounded, multi-stemmed, winter-hardy butterfly bush with long, densely-flowering, thyrse held from the soil line to the top of the plant beginning early in mid-summer and continuing over a long season until frost with sweetly-fragrant, orchid purple or red-purple flowers that are attractively offset by dark green foliage with silvery undersides.

1 Drawing Sheet

Botanical classification: *Buddleia davidii.*
Variety denomination: 'Orchid Annie'.

BACKGROUND OF THE PLANT

The present invention relates to the new and distinct butterfly bush plant of the Scrophulariaceae family, *Buddleia* 'Orchid Annie' hybridized by Hans A. Hansen in the summer of 2009 at a wholesale perennial nursery in Zeeland, Mich., USA. 'Orchid Annie' is the result of an ongoing breeding program conducted by the inventor. The goals for this program have been to produce improved, garden-worthy plants for the ornamental plant market. The new plant, originally assigned breeder code H9-47-01, is a single seedling selected from a self-pollination of *Buddleia* 'Blue Chip' U.S. Plant Pat. No. 19,991 as the female or seed patent and *Buddleia* 'Blue Chip' also as the male parent.

*Buddleia* 'Orchid Annie' was first asexually propagated from a single select plant in 2012 by stem cuttings at the same nursery in Zeeland, Mich. The resultant asexually propagated plants have been found to be stable and true to type in successive generations of asexual reproduction.

No plants of *Buddleia* 'Orchid Annie' have been sold, in this country or anywhere in the world, prior to the filing of this application, nor has any disclosure of the new plant been made prior to the filing of this application with the exception of that which may have been disclosed within one year of the filing of this application and was either derived directly or indirectly from the inventor.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

The following traits have been repeatedly observed and are determined to be the unique characteristics of 'Orchid Annie'.

The nearest comparison plants are *Buddleia* 'Blue Chip' U.S. Plant Pat. No. 19,991, 'Blue Chip Jr' U.S. Plant Pat. No. 26,581, 'Bosheven' U.S. Plant Pat. No. 25,707 and 'PIIBD-I' U.S. Plant Pat. No. 26,305. Compared to the female parent, 'Blue Chip', the new plant is shorter and has a more red-purple or orchid purple flower color compared to the blue flowers of 'Blue Chip'. Compared to 'Blue Chip Jr.' the new plant is slightly larger in habit and has a more red-purple or orchid purple flower color compared to the purple-violet of 'Blue Chip Jr.'. Compared to both 'Bosheven' and 'PIIBD-I' the new plant is significantly shorter and more compact in habit and has a slightly lighter and more reddish red-purple or orchid purple flower color.

*Buddleia* 'Orchid Annie' is a unique winter-hardy butterfly bush different from all other *Buddleia* cultivars known to the inventor based on the following combined traits:

1. Winter-hardy shrub, with multiple-stemmed, branched, compact, very short, round-mounded habit.
2. Many-flowered compact thyrse starting early and over a prolonged season beginning mid-summer and continuing until frost, from soil line to top of plant.
3. Sweetly fragrant flowers with orchid purple or red-purple petals.
4. Lanceolate foliage of dark green with silvery undersides.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
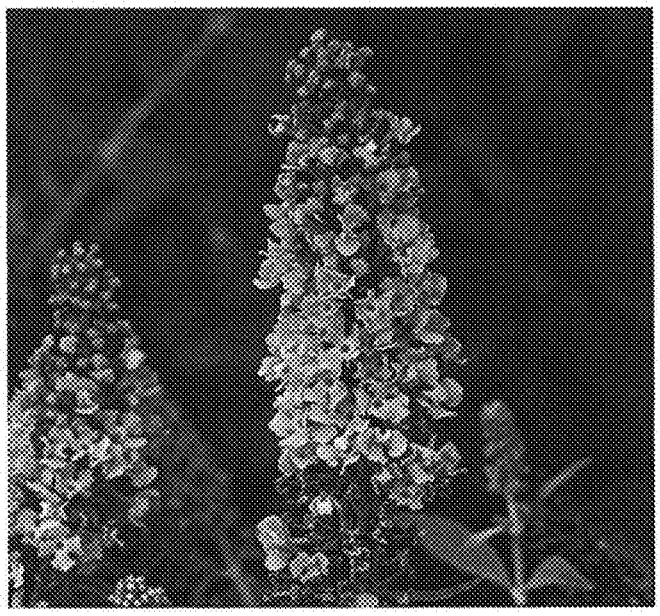
FIG. 1 shows a close-up of the flowers.
Figure 2:
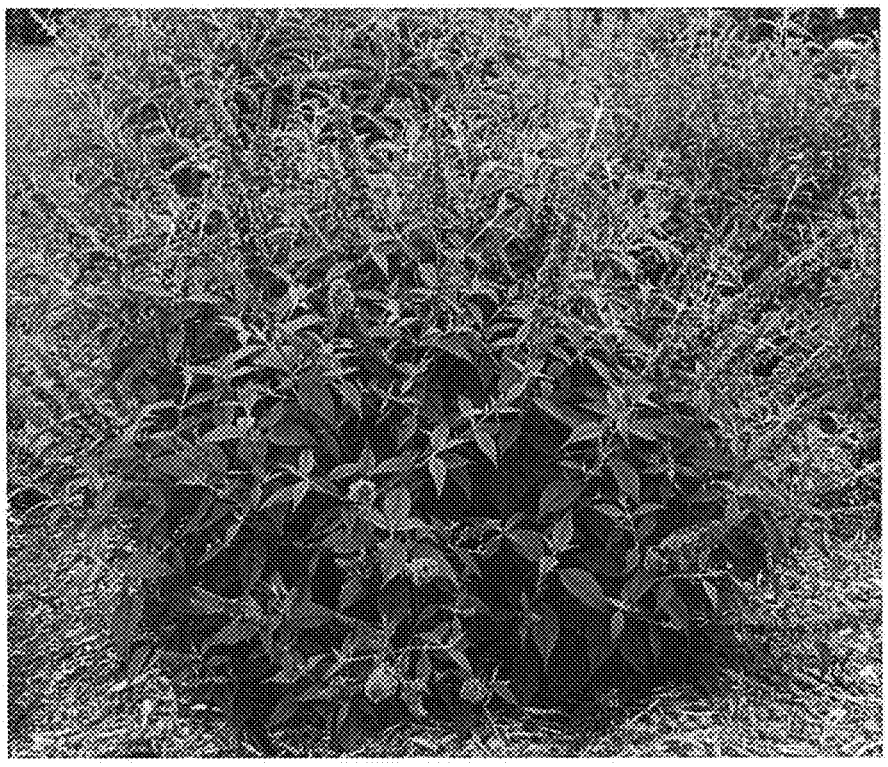
FIG. 2 shows the habit of a two-year-old plant in mid-season flowering.

The following descriptions and color references are based on the 2001 edition of The Royal Horticultural Society Colour Chart except where common dictionary terms are used. The new plant, *Buddleia* 'Orchid Annie', has not been observed under all possible environments. The phenotype may vary slightly with different environmental conditions, such as temperature, light, fertility, moisture and maturity levels, but without any change in the genotype. The following observations and size descriptions are of two-year-old plants in the loamy-sand, open-sun, field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in fall or early spring to promote new growth and flowering.

Parentage: *Buddleia* 'Blue Chip' as the female or seed parent times 'Blue Chip' as the male or pollen parent.

Propagation:

*Method*.—Softwood cuttings.

*Time to initiate roots from tissue culture*.—About two weeks.

*Rooting habit*.—Normal, dense and thick at base to about 1.5 cm diameter; fibrous, branching.

*Root color*.—Creamy white between RHS 159A and lighter than RHS 159 D depending on soil type.

*Crop time*.—Under normal spring growing conditions 6 to 7 weeks to fill and flower in a four-liter container a 65 mm liner; 8-10 weeks to finish and flower in a four-liter container from a 25 mm liner; Plant vigor is very good.

Plant description:

*Plant shape and habit*.—Winter-hardy, herbaceous, semi-woody, well-branched shrub with about 4 thick upright and branched main stems producing a compact rounded mound about 58 cm tall and about 50 cm wide.

*Stem*.—Woody and terete in cross section in lower portion with exfoliating bark; younger distal portion puberulent to canescent, quadrangular in cross section with ridges in corners; strong and flexible; average about 42 cm tall from soil line to just below terminal flowers, and about 0.8 cm diameter at the base; before distal flowers about 10 branches per main stem.

*Stem color*.—Distal portion while expanding nearest RHS 192B, just below flowers nearest RHS 138B with blush on areas exposed to intense sun nearest RHS N186C, ridges nearest RHS 138B, and in about basal 10 cm between RHS 200C and RHS 165B with striations between RHS 200A and RHS N199B.

*Plant size*.—Unpinched plant with stems flowering to about 58.0 cm tall; overall plant about 50.0 cm wide.

*Internode*.—About 10 nodes per stem below flowers, average internode length about 4.0 cm on unpinched plant; upper internodes slightly more elongated than lower internodes.

Foliage description: Opposite, decussate; serrulate; puberulent glabrous adaxial and canescent becoming puberulent with age abaxial; elliptic to lanceolate with attenuate base and acute apex; no foliar fragrance detected.

*Leaf blade size*.—Average about 5.0 cm long and about 18.0 mm wide; becoming smaller in distal portion of stem.

*Foliage color*.—Young expanding leaf blade base adaxial side nearest RHS 193C proximally and distally between RHS 137A and RHS 139A, young expanding abaxial between RHS N138C and RHS N138D; mature leaves adaxial side between RHS 139A and RHS 137A, abaxial more green than RHS 161C.

*Veins*.—Reticulate; abaxial raised, adaxial slightly impressed.

*Vein color*.—young expanding adaxial midrib and lateral veins same as surrounding blade; abaxial young expanding midrib nearest RHS 157A and lateral veins nearest RHS 155A; mature adaxial midrib and lateral veins nearest RHS 191C; abaxial midrib and lateral vein between RHS 193D and RHS 145D.

*Petioles*.—Glaucous and glabrous adaxial, pubescent abaxial; flatted partially on top; average size about 2.0 mm long and about 2.0 mm wide at the point of attachment to stem.

*Petiole color*.—Adaxial nearest RHS 138D and abaxial nearest RHS 145C.

*Inflorescence description*.—Glomerate thyrse consisting of about 400 self-cleaning salverform flowers; to about 20.0 cm long and about 6.0 cm across; beginning early in mid-July and continuing until late October or frost in Michigan.

*Buds*.—Elongated clavate, apex rounded with long straight base; one day prior to opening about 8.5 mm long and about 3.0 mm diameter in club and throat about 1.0 mm diameter in throat and about 6.0 mm long.

*Bud color*.—One day prior to opening nearest RHS N80A in club portion and tube portion blend between RHS N78A and RHS 70B.

*Sepals*.—Four; acute apex; proximal two-thirds connate; adpressed to corolla tube; glabrous adaxial and pubescent abaxial; margin entire, edentate; forming a corolla about 2.5 mm long and about 1.0 mm across; individually less than about 1.0 mm wide at point of fusion.

*Sepal color*.—Adaxial nearest RHS 137B, abaxial nearest RHS 138B with slight tinting of nearest RHS 183D.

*Flowers fragrance*.—Pleasantly and distinctly sweet.

*Flower attitude*.—Upward and outward.

*Lastingness of inflorescence*.—About 10 to 12 days.

*Lastingness of individual flower*.—About 3 to 6 days.

*Petals*.—Four; glabrous; fused into salverform with typically straight cylindrical tube about 8.0 mm long and 1.0 mm diameter, and a flattened face about 10.0 mm across; petal blade rounded apex with crenate margin; blade to about 3.0 mm across and about 3.1 mm long from fused face.

*Petal color*.—Adaxial tube base nearest RHS 1D, adaxial tube center blend of nearest RHS N172D and nearest RHS 184C in the tube surrounded by a thin irregular band of about 1.0 mm width of between RHS 23A and RHS 24A, adaxial face blades nearest RHS 70B; abaxial tube nearest RHS N25A and abaxial petal blades nearest RHS N78B.

*Gynoecium*.—Pistil: one; about 2.8 mm long. Style: short, terete, glabrous; about 1.5 mm long and less than 0.2 mm diameter; color nearest RHS 145C. Stigma: oblong, split in about distal 0.3 mm; minutely puberulent; about 0.5 mm in diameter and less than 0.7 mm long; color nearest RHS 144A. Ovary: superior; globose; about 1.0 mm across at base and 1.0 mm tall; distally tapering to style; color nearest RHS 144B.

*Androecium*.—Absent, none observed.

*Pedicel*.—Short, puberulent; about 1.5 mm long and about 0.5 mm diameter; color nearest RHS 139A.

*Peduncle*.—Quadrangular, pubescent, flexible and strong; flowering portion to about 20.0 cm long.

*Peduncle color*.—Nearest RHS 191B with tinting of nearest RHS N187B.

*Fruit and seed*.—Not observed.

Disease resistance: Resistance has been noted to deer browsing. Other resistance beyond that of known butterfly bush cultivars has not been observed. The plant grows best with plenty of moisture and adequate drainage, but is able to tolerate some drought when mature. Hardiness at least from USDA zone 6 through 10.

I claim:

1. A new cultivar of winter-hardy butterfly bush *Buddleia* plant named 'Orchid Annie' as herein illustrated and described, especially suitable for potted plant culture, landscaping as a specimen or en masse or as cut flower purposes.

* * * * *